(12) United States Patent
Dacquay et al.

(10) Patent No.: US 7,499,624 B2
(45) Date of Patent: Mar. 3, 2009

(54) OPHTHALMIC ENDOILLUMINATOR WITH VARIABLE-WEDGE ROTATING-DISK BEAM ATTENUATOR

(75) Inventors: Bruno Dacquay, Irvine, CA (US); John C. Huculak, Mission Viejo, CA (US); Ron T. Smith, Newport Coast, CA (US)

(73) Assignee: Alcon, Inc., Hunenberg (CH)

( * ) Notice: Subject to any disclaimer, the term of this patent is extended or adjusted under 35 U.S.C. 154(b) by 35 days.

(21) Appl. No.: 11/687,342

(22) Filed: Mar. 16, 2007

(65) Prior Publication Data

US 2008/0225232 A1      Sep. 18, 2008

(51) Int. Cl.
*G02B 6/00* (2006.01)
*A61B 1/06* (2006.01)

(52) U.S. Cl. ...................... 385/140; 600/182

(58) Field of Classification Search .................. 385/140
See application file for complete search history.

(56) References Cited

U.S. PATENT DOCUMENTS

| 3,016,800 | A |   | 1/1962  | Pliskin |
|---|---|---|---|---|
| 3,775,606 | A |   | 11/1973 | Bazell et al. |
| 4,061,911 | A |   | 12/1977 | Krasin |
| 4,233,650 | A |   | 11/1980 | Hagner et al. |
| 4,356,534 | A |   | 10/1982 | Hattori et al. |
| 4,397,523 | A |   | 8/1983  | Feinbloom et al. |
| 4,425,599 | A | * | 1/1984  | Rieder et al. ................. 362/552 |
| 4,439,024 | A |   | 3/1984  | Ito |
| 4,608,622 | A |   | 8/1986  | Gonser |
| 4,623,217 | A |   | 11/1986 | Hallen |
| 4,628,416 | A |   | 12/1986 | Dewey |
| 4,757,426 | A |   | 7/1988  | Scheller et al. |
| 4,811,182 | A |   | 3/1989  | Solomon |
| 5,053,934 | A |   | 10/1991 | Krebs |
| 5,217,285 | A |   | 6/1993  | Sopori |
| 5,281,984 | A |   | 1/1994  | Burton et al. |
| 5,382,987 | A |   | 1/1995  | Sperling |
| 5,510,969 | A |   | 4/1996  | Rodger et al. |
| 5,658,070 | A | * | 8/1997  | Rowe et al. ................. 362/283 |
| 6,367,958 | B1 | * | 4/2002 | Jones ......................... 362/552 |

FOREIGN PATENT DOCUMENTS

| EP | 0611547 A1 | 8/1994 |
|---|---|---|
| JP | 5232387 | 10/1993 |
| WO | WO 92/11548 | 7/1992 |

OTHER PUBLICATIONS

Grieshaber & Co. Inc., "G.L.S. The Grieshaber Light Source", brochure, 1990.

* cited by examiner

*Primary Examiner*—Uyen Chau N Le
*Assistant Examiner*—Kajli Prince
(74) *Attorney, Agent, or Firm*—Kenneth D. Bassinger

(57) ABSTRACT

An ophthalmic endoilluminator includes a light source, a variable-wedge rotating-disk attenuator, a condensing lens, and an optical fiber. The variable-wedge rotating-disk attenuator attenuates the light produced by the light source. The variable-wedge rotating-disk attenuator includes a wedge capable of being adjusted over a variable angle as measured through an arc of the wedge and an axle to which the wedge is attached. The axle rotates such that the wedge rotates around a pivot defined by the axle. The condensing lens focuses the attenuated light. The optical fiber carries the focused light into an eye. The variable-wedge rotating-disk attenuator is located such that it affects the intensity of a light beam transmitted into an eye.

24 Claims, 5 Drawing Sheets

OPHTHALMIC ENDOILLUMINATOR WITH VARIABLE-WEDGE ROTATING-DISK BEAM ATTENUATOR

BACKGROUND OF THE INVENTION

The present invention relates to an illuminator for use in ophthalmic surgery and more particularly to ophthalmic illuminator utilizing a variable-wedge rotating-disk attenuator to produce a light suitable for illuminating the inside of the eye.

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. Since such lamps cannot be easily dimmed while maintaining output performance and color balance, they are run at full power, and light intensity is varied by mechanical means. In varying the intensity of the light beam, it is important to maintain the beam diameter and only decrease the intensity of the beam. The light beam, whether attenuated or not, must be focused and aligned with the optical fiber that carries the beam into the eye.

Traditionally, the intensity of the light is varied by using mechanical louvers, camera variable aperture mechanisms, or neutral density filters. A mechanical louver operates like a set of Venetian blinds. The louvers are opened a certain amount to allow a certain amount of light to pass through. Such louvers, however, produce a series of bright and dark stripes in the resulting light beam. These can result in rings and other angular non-uniformities that appear in the beam emitted from the optical fiber. These non-uniformities deteriorate the quality of intraocular illumination. Likewise, the use of mechanical variable aperture mechanisms can also cause angular non-uniformities and an undesired narrowing of the width of the beam exiting the distal end of the fiber. Neutral density filters are often made of glass and block unwanted light. As they block light, they can heat up and crack. What is needed is an attenuator that does not decrease the diameter of the light beam or produce non-uniformities.

SUMMARY OF THE INVENTION

In one embodiment consistent with the principles of the present invention, the present invention is an ophthalmic endoilluminator with a light source, a collimating lens, a cold mirror, an attenuator, a condensing lens, and an optical fiber. The collimating lens collimates the light produced by the light source. The cold mirror reflects a portion of the collimated light. The attenuator is a variable-wedge rotating-disk attenuator for attenuating the light reflected from the cold mirror. The condensing lens focuses the attenuated light. The optical fiber carries the focused light into an eye.

In another embodiment consistent with the principles of the present invention, the present invention is an ophthalmic endoilluminator including a light source, a variable-wedge rotating-disk attenuator, a condensing lens, and an optical fiber. The variable-wedge rotating-disk attenuator attenuates the light produced by the light source. The variable-wedge rotating-disk attenuator includes a wedge capable of being adjusted over a variable angle as measured through an arc of the wedge and an axle to which the wedge is attached. The axle rotates such that the wedge rotates around a pivot defined by the axle. The condensing lens focuses the attenuated light. The optical fiber carries the focused light into an eye. The variable-wedge rotating-disk attenuator is located such that it affects the intensity of a light beam transmitted into an eye.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
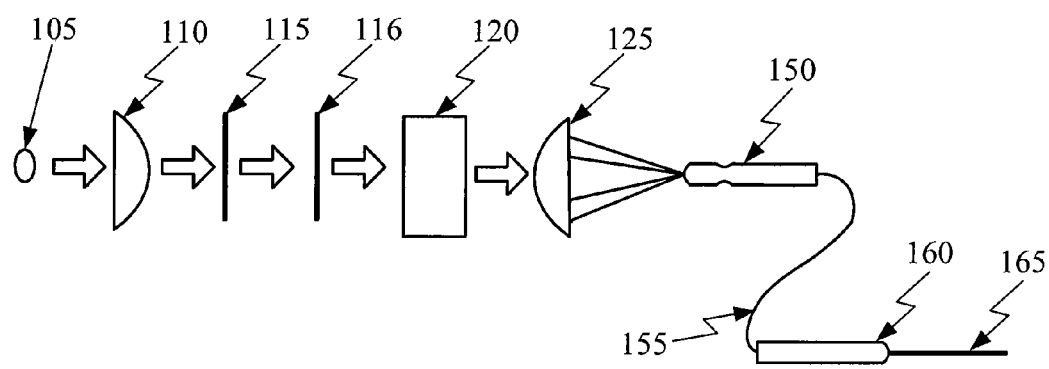
FIG. 1 is an unfolded view of an ophthalmic endoilluminator according to an embodiment of the present invention.

FIG. 1 is an unfolded view of an ophthalmic endoilluminator according to an embodiment of the present invention. In FIG. 1, the endoilluminator includes light source 105, collimating lens 110, optional cold mirror 115, optional hot mirror 116, attenuator 120, condensing lens 125, connector 150, optical fiber 155, hand piece 160, and probe 165.

The light from light source 105 is collimated by collimating lens 110. The collimated light is reflected and filtered by optional cold mirror 115 and/or optional hot mirror 116. The resulting beam is attenuated by attenuator 120 and focused by condensing lens 125. The focused beam is directed through connector 150 and optical fiber 155 to probe 165 where it illuminates the inside of the eye.

Light source 105 is typically a lamp, such as a mercury vapor lamp, a xenon lamp, a metal halide lamp, or a halogen lamp. Light source 105 is operated at or near full power to produce a relatively stable and constant light output. Other embodiments of the present invention utilize other light sources such as light emitting diodes (LEDs). One or more LEDs can be operated to produce a constant and stable light output. As is known, there are many types of LEDs with different power ratings and light output that can be selected as light source 105.

Collimating lens 110 is configured to collimate the light produced by light source 105. As is commonly known, collimation of light involves lining up light rays. Collimated light is light whose rays are parallel with a planar wave front. Other collimating elements, besides collimating lens 110 may also be employed. For example, an aspheric lens, a set of spherical lenses, or a hybrid refractive-diffractive lens may be used to collimate light.

Optional cold mirror 115 is a dichroic reflector that reflects visible wavelength light and only transmits infrared and ultraviolet light to produce a beam filtered of harmful infrared and ultraviolet rays. Optional hot mirror 116 reflects long wavelength infrared light and short wavelength ultraviolet light while transmitting visible light. The eye's natural lens filters the light that enters the eye. In particular, the natural lens absorbs blue and ultraviolet light which can damage the retina. Providing light of the proper range of visible light wavelengths while filtering out harmful short and long wavelengths can greatly reduce the risk of damage to the retina through aphasic hazard, blue light photochemical retinal damage and infrared heating damage, and similar light toxicity hazards. Typically, a light in the range of about 430 to 700 nanometers is preferable for reducing the risks of these hazards. Optional cold mirror 115 and optional hot mirror 116 selected to allow light of a suitable wavelength to be emitted into an eye. Other filters and/or dichroic beam splitters may also be employed to produce a light in this suitable wavelength range. For example, holographic mirrors may also be used to filter light.

Attenuator 120 attenuates or decreases the intensity of the light beam as more fully described in the following Figures.

Condensing lens 125 focuses the attenuated light beam so that it can be launched in to a small gauge optical fiber. Condensing lens 125 is a lens of suitable configuration for the system. Condensing lens 125 is typically designed so that the resulting focused beam of light can be suitably launched into and transmitted by an optical fiber. As is commonly known, a condensing lens may be a biconvex or a plano-convex aspheric lens where one surface is planar and the other surface is convex with a precise aspheric surface in order to focus the light to a minimum diameter spot. In addition, condensing lens may also be a hybrid refractive-diffractive lens.

The endoilluminator that is handled by the ophthalmic surgeon includes connector 150, optical fiber 155, hand piece 160, and probe 165. Connector 150 is designed to connect the optical fiber 155 to a main console (not shown) containing light source 105. Connector 150 properly aligns optical fiber 155 with the beam of light that is to be transmitted into the eye. Optical fiber 155 is typically a small gauge fiber that may or may not be tapered. Hand piece 160 is held by the surgeon and allows for the manipulation of probe 165 in the eye. Probe 165 is inserted into the eye and carries optical fiber 155 which terminates at the end of probe 165. Probe 165 thus provides illumination from optical fiber 155 in the eye.

Figure 2A:
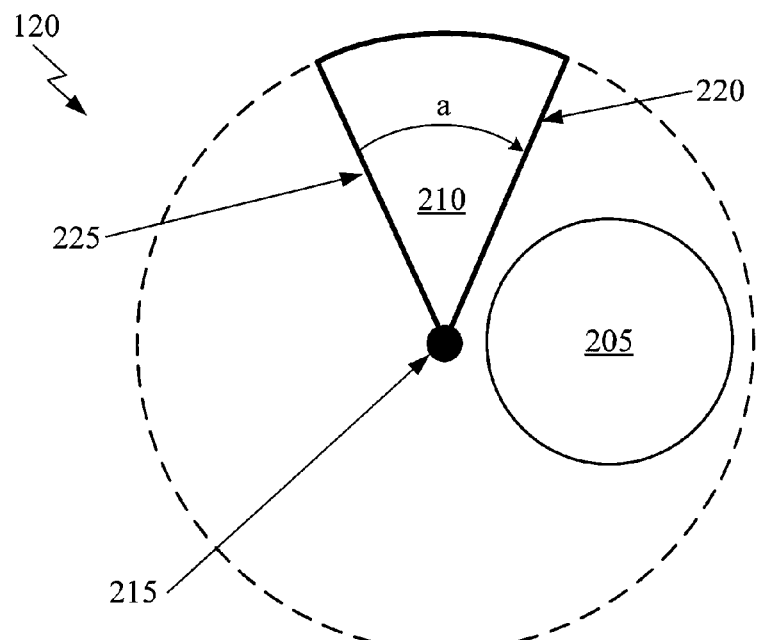
FIGS. 2A-2D are various views of a variable-wedge rotating-disk attenuator according to an embodiment of the present invention.

FIG. 2A is a view of a variable-wedge rotating-disk attenuator according to an embodiment of the present invention. Attenuator 120 includes a variable wedge 210 of an angle "a" that rotates around pivot 215. Variable wedge 210 is bounded by two spines 220 and 225. These two spines 220 and 225 support opaque material that makes up variable wedge 210. Light beam 205 is depicted as well. While variable wedge 210 is depicted as being pie-shaped, it can be of any convenient shape, such as, for example, a triangle.

Variable wedge 210 can be adjusted so that angle "a" is in the range of nearly zero degrees to 360 degrees. In one embodiment, variable wedge 210 operates like a Japanese fan that can be opened to form a complete disc or closed to form a very narrow wedge. Variable wedge 210 typically includes segmented members (located between spines 220 and 225 in FIG. 2A) that can be folded together to decrease angle "a" or unfolded to increase angle "a." These members of variable wedge 210 are made of a substantially optically opaque material designed to block light. This material may block 100% of the light or less than 100% of the light.

Variable wedge 210 is attached to a rotating axle, the end of which is seen as pivot 215. The axle and attached variable wedge 210 is rotated rapidly so as to periodically occlude beam 205. The variable wedge 210 is rotated more rapidly than the human eye can see, typically at a rate of greater than sixty times per second. Beam 205 is attenuated in proportion to the size of variable wedge 210. The greater the angle "a," the more attenuation occurs.

A controller (not shown) controls the operation of the variable-wedge rotating-disk attenuator 120, a power supply (not shown) provides power to operate the variable-wedge rotating-disk attenuator 120, and a motor (not shown) rotates the axle. The controller controls the operation of the various components of the system and is typically an integrated circuit with power, input, and output pins capable of performing logic functions. In various embodiments, the controller is a targeted device controller performing specific control functions targeted to a specific device or component, such as directing the operation of the variable-wedge rotating-disk attenuator 120. In other embodiments, the controller is a programmable microprocessor. Software loaded into the microprocessor implements the control functions provided by the controller. The controller may be made of many different components or integrated circuits. The power supply may be, for example, a switch mode power supply or other type of power supply.

Using variable wedge 210 to attenuate light beam 205 eliminates the non-uniformities produced by prior art means of attenuation. Variable wedge 210 occludes light beam 205 and therefore does not reduce its diameter. In addition, variable wedge 210 does not produce striations or lines in light beam 205. As such, the resulting intraocular light is of a higher quality.

Figure 2B:
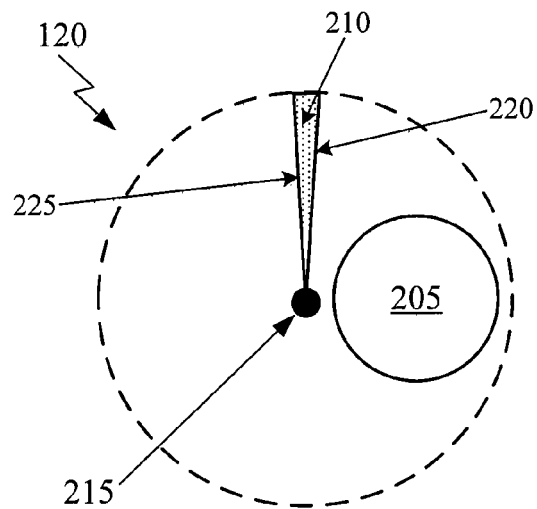
Figure 2C:
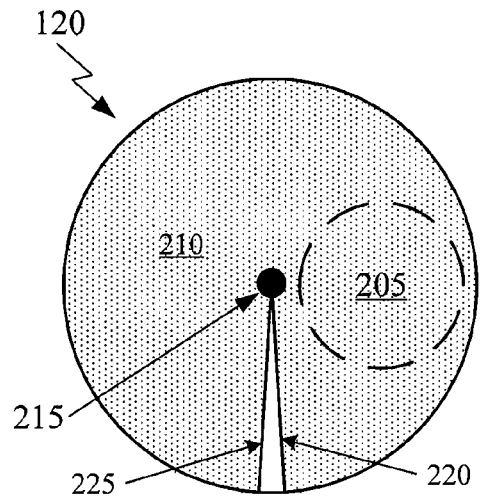

FIGS. 2B and 2C are two different views of the variable-wedge rotating-disk attenuator of FIG. 2A according to an embodiment of the present invention. In FIG. 2B variable wedge 210, denoted by the shaded area, is small (angle "a" is small), and in FIG. 2C, variable wedge 210, denoted by the shaded area, is large (angle "a" is large). In FIG. 2B, light beam 205 is minimally occluded, and in FIG. 2C, light beam is almost totally occluded. In this manner, angle "a" can be adjusted to vary the size of variable wedge 210 to produce almost no attenuation up to a complete attenuation of light beam 205. The resulting intraocular light can thus be varied from no light to a maximum light.

Figure 2D:
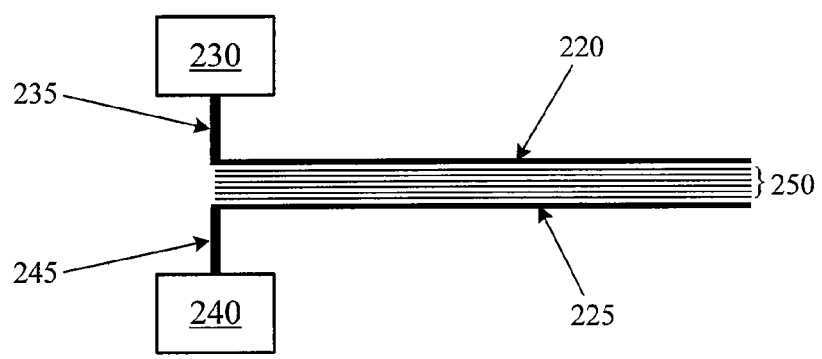

FIG. 2D shows a top view of the variable wedge attenuator of FIGS. 2A-2C. In FIG. 2D, spines 220 and 225 support opaque material members 250 that form the various segments of the fan-like structure of variable wedge 210. Axle 235 is connected to spine 220 at a substantially right angle. Likewise, axle 245 is connected to spine 225 at a substantially right angle. Axles 235 and 245 are connected to and driven by motors 230 and 240, respectively. In this manner, motor 230 rotates axle 235 which in turn drives spine 220 in a circular direction, and motor 240 rotates axle 245 which in turn drives spine 225 in a circular direction. Motors 230 and 240 are synchronized but out of phase. In other words, both motors 230 and 240 are driven at the same rotational rate of speed, while the phase angle between them corresponds to angle "a"—the angle between spines 220 and 225. A controller (not shown) as described above controls the operation of motors, 230 and 240.

Figure 3A:
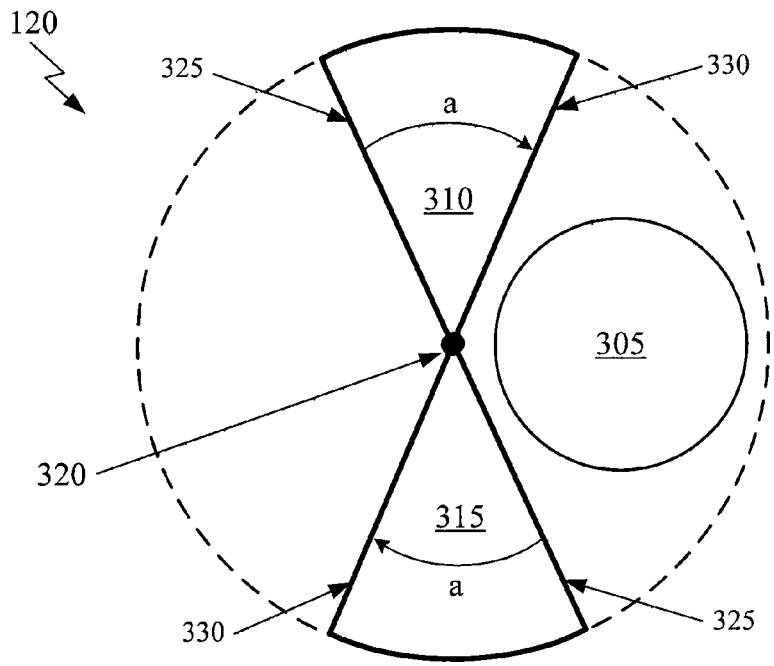
FIGS. 3A-3D are various views of a variable-wedge rotating-disk attenuator according to an embodiment of the present invention.

FIGS. 3A-3D depict a variable-wedge rotating-disk attenuator with two wedges according to an embodiment of the present invention. The structure and operation of the embodiment of FIGS. 3A-3D is similar to that of FIGS. 2A-2D. In FIG. 3A, attenuator 120 includes two variable wedges, 310 and 315, each of angle "a." These two wedges are located opposite each other with respect to pivot 320 and rotate around pivot 320. Variable wedges 310 and 315 are bounded by two spines 325 and 330. The approximate center of each spine is located at pivot 320. These two spines 325 and 330 support opaque material that makes up variable wedges 310 and 315. Light beam 305 is depicted as well. While variable wedges 310 and 315 are depicted as being pie-shaped, they can be of any convenient shape, such as, for example, a triangle.

Variable wedges 310 and 315 can be adjusted so that angle "a" is in the range of nearly zero degrees to 360 degrees. In one embodiment, variable wedges 310 and 315 operate like a Japanese fan that can be opened to form a complete disc or closed to form a very narrow wedge. Variable wedges 310 and 315 typically include segmented members (located between spines 325 and 330) that can be folded together to decrease angle "a" to nearly zero degrees or unfolded to increase angle "a" to 180 degrees. These members of variable wedges 310 and 315 are made of a substantially optically opaque material designed to block light. This material may block 100% of the light or less than 100% of the light.

Variable wedges 310 and 315 are attached to a rotating axle, the end of which is seen as pivot 320. The axle and attached variable wedges 310 and 315 are rotated rapidly so as to periodically occlude beam 305. The variable wedges 310 and 315 are rotated more rapidly than the human eye can see, typically at a rate of greater than sixty times per second. Beam 305 is attenuated in proportion to the size of the variable wedges 310 and 315. The greater the angle "a," the more attenuation occurs.

A controller (not shown) controls the operation of the variable-wedge rotating-disk attenuator 120, a power supply (not shown) provides power to operate the variable-wedge rotating-disk attenuator 120, and a motor (not shown) rotates the axle. The controller controls the operation of the various components of the system and is typically an integrated circuit with power, input, and output pins capable of performing logic functions. In various embodiments, the controller is a targeted device controller performing specific control functions targeted to a specific device or component, such as directing the operation of the variable-wedge rotating-disk attenuator 120. In other embodiments, the controller is a programmable microprocessor. Software loaded into the microprocessor implements the control functions provided by the controller. The controller may be made of many different components or integrated circuits. The power supply may be, for example, a switch mode power supply or other type of power supply.

Using variable wedges 310 and 315 to attenuate light beam 305 eliminates the non-uniformities produced by prior art means of attenuation. Variable wedges 310 and 315 occlude light beam 305 and therefore do not reduce its diameter. In addition, variable wedges 310 and 315 do not produce striations or lines in light beam 305. As such, the resulting intraocular light is of a higher quality.

Figure 3B:
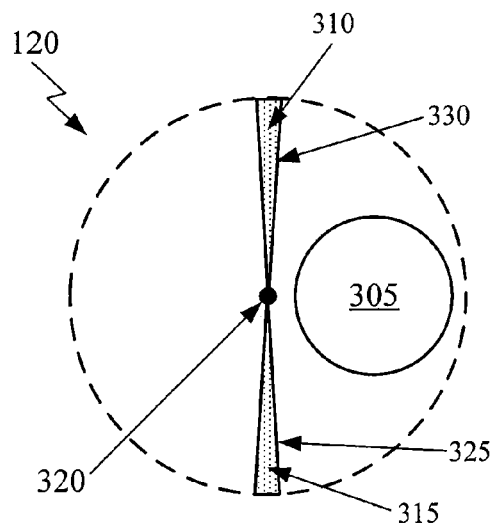
Figure 3C:
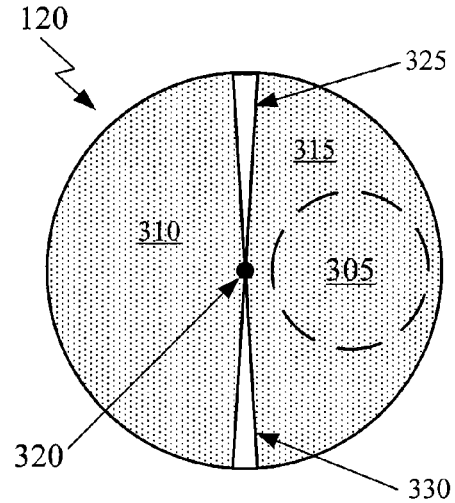

FIGS. 3B and 3C are two different views of the variable-wedge rotating-disk attenuator of FIG. 3A according to an embodiment of the present invention. In FIG. 3B variable wedges 310 and 315, denoted by the shaded area, are small (angle "a" is small), and in FIG. 3C, variable wedges 310 and 315, denoted by the shaded area, are large (angle "a" is large). In FIG. 3B, light beam 305 is minimally occluded, and in FIG. 3C, light beam is almost totally occluded. In this manner, angle "a" can be adjusted to vary the size of variable wedges 310 and 315 to produce almost no attenuation up to a complete attenuation of light beam 305. The resulting intraocular light can thus be varied from no light to a maximum light.

Figure 3D:
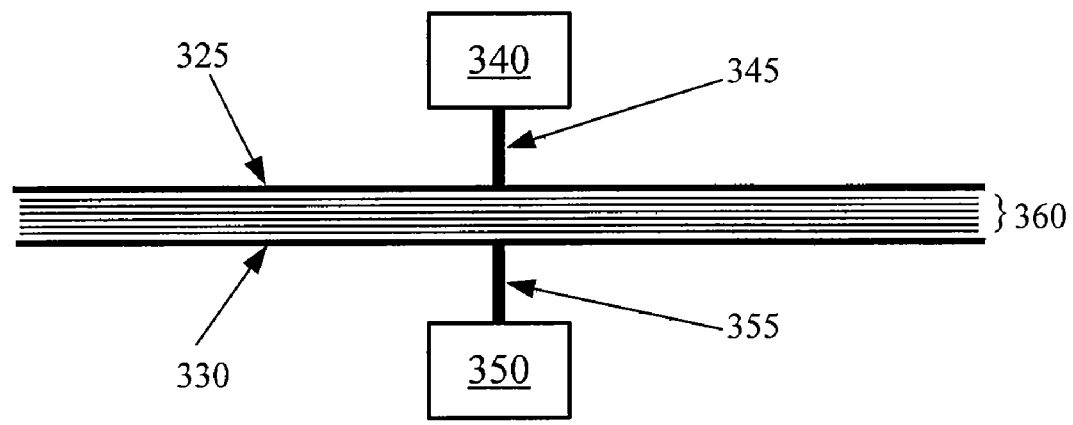

FIG. 3D shows a top view of the variable wedge attenuator of FIGS. 3A-3C. In FIG. 3D, spines 325 and 330 support opaque material members 360 that form the various segments of the fan-like structure of variable wedges 310 and 315. Axle 345 is connected to spine 325 at a substantially right angle. Likewise, axle 355 is connected to spine 330 at a substantially right angle. Axles 345 and 355 are aligned with pivot 320. Axles 345 and 355 are connected to and driven by motors 340 and 350, respectively. In this manner, motor 340 rotates axle 345 which in turn drives spine 325 in a circular direction, and motor 350 rotates axle 355 which in turn drives spine 330 in a circular direction. Motors 340 and 350 are synchronized but out of phase. In other words, both motors 340 and 350 are driven at the same rotational rate of speed, while the phase angle between them corresponds to angle "a"—the angle between spines 325 and 330. A controller (not shown) as described above controls the operation of motors 340 and 350.

The embodiment of FIGS. 3A-3D is balanced around pivot 320. In other words, the mass of variable wedge 310 is roughly equal to the mass of variable wedge 315. Variable wedge 310 is also located opposite variable wedge 315. When driven by motors 340 and 350, the attenuator is a balanced system.

Other numbers of variable wedges can be utilized in the same manner described in FIGS. 3A-3D. For example, Attenuator 120 may include three, four, or any number of wedges equally spaced around pivot 320. Three wedges require three spines; four wedges require four spines, etc. The number of wedges is limited only by the physical space requirements for a given system. These multiple wedge attenuators can be operated in the same manner as that described in FIGS. 3A-3D. For example, in a four wedge system with four spines, two spines can be disposed at right angles to each other and driven by one motor, while the other two spines can be disposed at right angles to each other and driven by the other motor.

Figure 5:
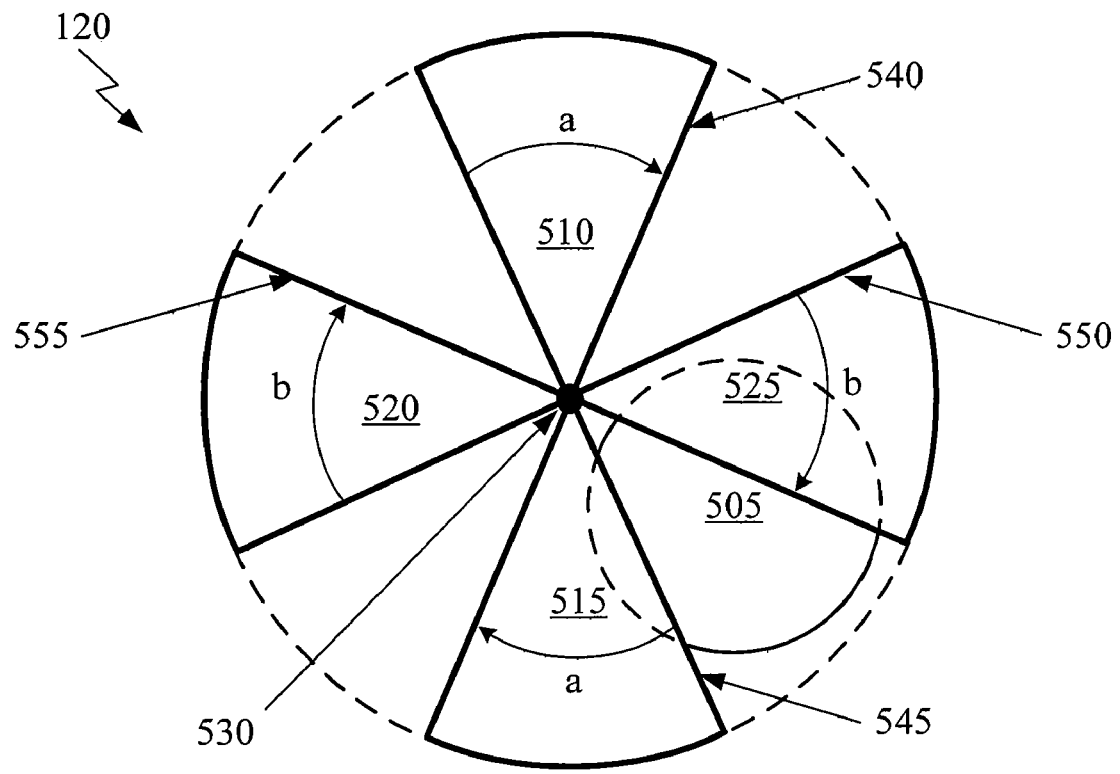
FIG. 5 depicts a variable-wedge rotating-disk attenuator with four wedges according to an embodiment of the present invention.

For example, in FIG. 5, four variable wedges 510, 515, 520, and 525 are employed in attenuator 120. Light beam 505 is partially occluded by variable wedges 515 and 525. Variable wedges 510 and 515 are bounded by spines 540 and 545 and have the same angle "a." Likewise, variable wedges 520 and 525 are bounded by spines 550 and 555 and have the same angle "b." Spine 545 is arranged to be at a substantially right angle to spine 550. Likewise, spine 540 is arranged to be at a substantially right angle to spine 555. Spines 545 and 550 can be connected via an axle to one motor, and spines 540 and 555 can be connected to via another axle to another motor. The axles can be aligned with pivot point 530. The attenuator 120 of FIG. 5 can be operated in the same manner as the attenuator in FIG. 3A.

Figure 6:
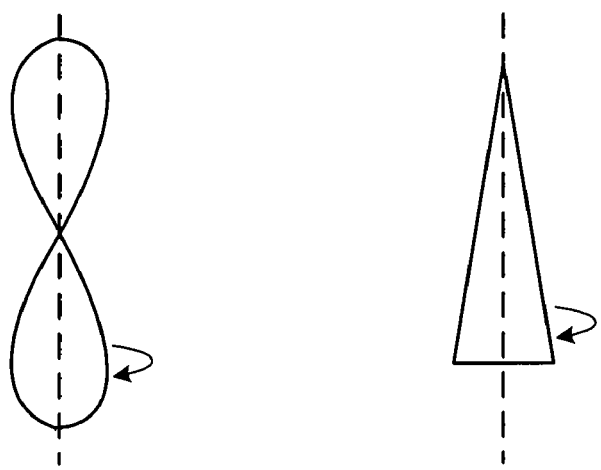
FIG. 6 depicts a propeller blade and a triangular blade that can be utilized with a variable-wedge rotating-disk attenuator with four wedges according to an embodiment of the present invention.

In addition to a wedge design, FIG. 6 depicts a propeller and a triangle that can be implemented in attenuator 120. The blades of the propeller can be rotated about the central pivot point as well as about an axis denoted by the dashed line. In this manner, the propeller blades can be fixed at an angle with respect to the dashed line (like the blades of an airplane propeller or a ceiling fan) to occlude a certain percentage of the light beam. This angle can be varied to occlude more or less light. The same principle can be used for other shapes, such as the triangle. These propellers and triangular blades can be used as wedges or variable wedges in the present invention.

Figure 4:
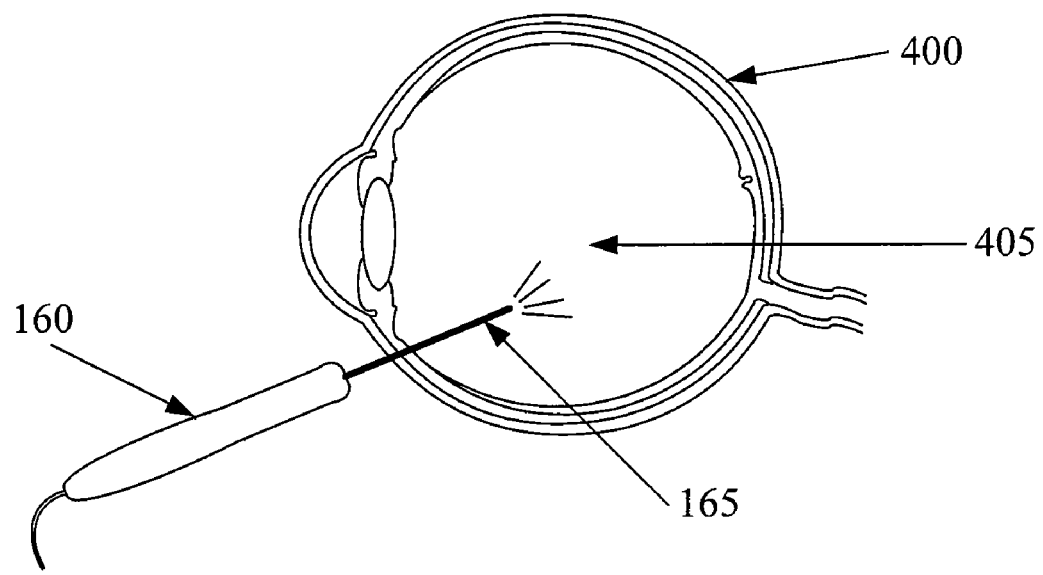
FIG. 4 is a cross section view of an ophthalmic endoilluminator located in an eye according to an embodiment of the present invention.

FIG. 4 is cross section view of an ophthalmic endoilluminator located in an eye according to an embodiment of the present invention. FIG. 4 depicts hand piece 160 and probe 165 in use. Probe 165 is inserted into eye 400 through an incision in the pars plana region. Probe 165 illuminates the inside or vitreous region 405 of eye 400. In this configuration, probe 165 can be used to illuminate the inside or vitreous region 405 of eye 400 during vitreo-retinal surgery.

From the above, it may be appreciated that the present invention provides an improved system for illuminating the inside of the eye. The present invention provides a light source that can be attenuated without distortion or a reduction in beam size to provide a light suitable for illuminating the inside of an eye. A variable-wedge rotating-disk attenuator is operated to alter the intensity of the light beam entering the eye without causing unwanted non-uniformities. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic endoilluminator comprising:
 a light source for producing light;
 a collimating element for collimating the light produced by the light source;
 a variable-wedge rotating-disk attenuator for attenuating the collimated light, the variable-wedge rotating disk attenuator comprising a wedge capable of being adjusted over a variable angle as measured through an arc of the wedge and an axle to which the wedge is attached, the axle capable of rotating such that the wedge rotates around a pivot defined by the axle;
 a condensing element for focusing the attenuated light; and
 an optical fiber for carrying the focused light into an eye.

2. The endoilluminator of claim 1 further comprising:
 a filter for filtering unwanted wavelengths from the collimated light.

3. The endoilluminator of claim 2 wherein the filter comprises a cold mirror.

4. The endoilluminator of claim 2 wherein the filter comprises a hot mirror.

5. The endoilluminator of claim 1 wherein the condensing element comprises a lens.

6. The endoilluminator of claim 1 wherein the collimating element comprises a lens.

7. The endoilluminator of claim 1 further comprising:
 a power supply coupled to the light source.

8. The endoilluminator of claim 1 further comprising:
 a connector for aligning the attenuated light with the optical fiber;
 a hand piece carrying the optical fiber, the hand piece capable of being manipulated in the hand; and
 a probe for carrying the optical fiber into the eye.

9. The endoilluminator of claim 1 further comprising:
 a controller for controlling an operation of the variable-wedge rotating disk attenuator.

10. The endoilluminator of claim 1 wherein the variable-wedge rotating disk attenuator controls an intensity of the focused light.

11. The endoilluminator of claim 1 wherein the wedge is pie-shaped.

12. The endoilluminator of claim 1 wherein the wedge comprises movable segments.

13. The endoilluminator of claim 1 further comprising:
 a motor coupled to the axle.

14. The endoilluminator of claim 1 further comprising:
 a controller for controlling the size of the wedge.

15. The endoilluminator of claim 1 further comprising:
 a controller for controlling a rotation of the axle.

16. An ophthalmic endoilluminator comprising:
 a light source for producing light;
 a variable-wedge rotating-disk attenuator for attenuating the light produced by the light source, the variable-wedge rotating-disk attenuator comprising a first wedge capable of being adjusted over a variable angle as measured through an arc of the first wedge, a second wedge, and an axle to which the first and second wedges are attached, the axle capable of rotating such that the first and second wedges rotate around a pivot defined by the axle;

a condensing lens for focusing the attenuated light; and an optical fiber for carrying the focused light into an eye wherein the variable-wedge rotating-disk attenuator is located such that it affects the intensity of a light beam transmitted into an eye.

17. The endoilluminator of claim 16 further comprising:
a collimating lens for collimating the light produced by the light source.

18. The endoilluminator of claim 17 further comprising:
a filter for filtering unwanted wavelengths from the collimated light.

19. The endoilluminator of claim 16 further comprising:
a power supply coupled to the light source.

20. The endoilluminator of claim 16 further comprising:
a connector for aligning the attenuated light with the optical fiber;
a hand piece carrying the optical fiber, the hand piece capable of being held in the hand; and
a probe for carrying the optical fiber into the eye.

21. The endoilluminator of claim 16 further comprising:
a controller for controlling an operation of the variable-wedge rotating disk attenuator.

22. The endoilluminator of claim 16 wherein the first wedge is pie-shaped.

23. The endoilluminator of claim 16 wherein the first wedge comprises movable segments.

24. The endoilluminator of claim 16 further comprising:
a motor coupled to the axle.

* * * * *